(12) United States Patent
Bauer

(10) Patent No.: US 8,185,190 B2
(45) Date of Patent: May 22, 2012

(54) ASSESSMENT OF ISCHEMIA, AND RISK OF SUDDEN CARDIAC DEATH, VIA HEART-FUNCTIONALITY PARAMETER AND ACOUSTIC CARDIOGRAPHIC MONITORING

(75) Inventor: Peter T. Bauer, West Linn, OR (US)

(73) Assignee: Inovise Medical, Inc., Portland, OR (US)

( * ) Notice: Subject to any disclaimer, the term of this patent is extended or adjusted under 35 U.S.C. 154(b) by 472 days.

(21) Appl. No.: 12/321,646

(22) Filed: Jan. 23, 2009

(65) Prior Publication Data

US 2009/0204167 A1 Aug. 13, 2009

Related U.S. Application Data

(60) Provisional application No. 61/062,702, filed on Jan. 29, 2008.

(51) Int. Cl.
*A61B 5/04* (2006.01)
*A61B 5/02* (2006.01)

(52) U.S. Cl. .................. 600/509; 600/514; 600/528

(58) Field of Classification Search .................. 600/509, 600/514, 528; 607/9, 17
See application file for complete search history.

(56) References Cited

U.S. PATENT DOCUMENTS

| | | | |
|---|---|---|---|
| 5,392,780 A | 2/1995 | Ogino et al. | |
| 7,039,538 B2 | 5/2006 | Baker, Jr. | |
| 7,174,203 B2 | 2/2007 | Arand et al. | |
| 7,225,021 B1 | 5/2007 | Park et al. | |
| 7,559,903 B2 | 7/2009 | Moussavi et al. | |
| 2004/0127792 A1* | 7/2004 | Siejko et al. | .............. 600/439 |
| 2005/0027323 A1 | 2/2005 | Mulligan et al. | |
| 2006/0155202 A1 | 7/2006 | Arand et al. | |
| 2007/0038137 A1 | 2/2007 | Arand et al. | |
| 2008/0021510 A1 | 1/2008 | Mi et al. | |
| 2008/0177191 A1 | 7/2008 | Patangay et al. | |
| 2009/0165559 A1 | 7/2009 | Lec | |

OTHER PUBLICATIONS

International Search Report, Serial No. PCT/US10/055696, dated Dec. 23, 2010, 13 pages total.
USPTO Office Action, U.S. Appl. No. 12/315,165, dated Nov. 12, 2010, 9 pages total.
USPTO Office Action, U.S. Appl. No. 11/264,328, dated May 9, 2008, 7 pages total.
USPTO Office Action, U.S. Appl. No. 11/264,328, dated Oct. 16, 2008, 8 pages total.
USPTO Office Action for U.S. Appl. No. 12/321,647 dated Jun. 1, 2011. 7pp.
USPTO Office Action for U.S. Appl. No. 12/288,712 dated Apr. 11, 2011. 5pp.
USPTO Office Action for U.S. Appl. No. 12/321,650 dated Sep. 7, 2011. 8pp.

* cited by examiner

*Primary Examiner* — Nicole F Lavert
(74) *Attorney, Agent, or Firm* — Jon M. Dickinson, Esq.; Robert D. Varitz, Esq.

(57) ABSTRACT

Methodology involving assessing, and applying therapy regarding, degree of ischemia and risk for sudden cardiac death in a therapy-device-equipped subject utilizing a Holter-type instrumentality. The methodology includes (a) gathering simultaneous ECG and heart-sound data, (b) computer processing and interrelating the gathered data to obtain one or more heart-functionality parameter(s), focusing on LDPT and % LVST, and (c), using these obtained parameters, adjusting, as necessary, the therapy device so as to minimize and counteract the likelihood of the onset or advancement of ischemia, and/or the onset of sudden cardiac death.

8 Claims, 4 Drawing Sheets

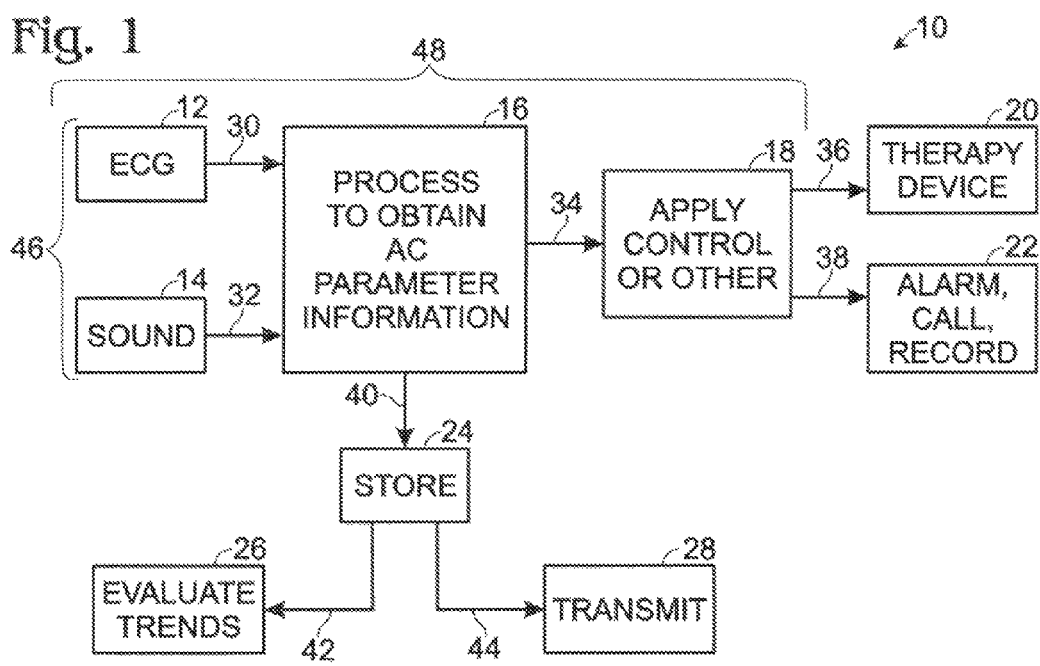
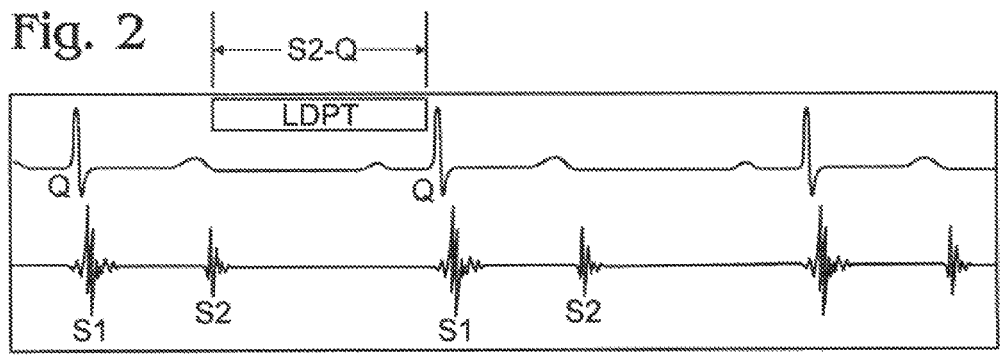

ASSESSMENT OF ISCHEMIA, AND RISK OF SUDDEN CARDIAC DEATH, VIA HEART-FUNCTIONALITY PARAMETER AND ACOUSTIC CARDIOGRAPHIC MONITORING

CROSS-REFERENCES TO RELATED APPLICATIONS, AND ISSUED PATENT

This patent application claims priority from U.S. Provisional Patent Application Ser. No. 61/062,702, filed Jan. 29, 2008, for Stage-Monitored Physiologic-Demand Heart Pacing, and also relates to subject matter presented (a) in U.S. patent application Ser. No. 11/264,328, filed Nov. 1, 2005 for Hemodynamic Assessment/Adjustment, now abandoned, (b) in U.S. patent application Ser. No. 11/442,467, filed May 25, 2006, for Cardio-Function Cafeteria System and Methodology, also now abandoned and (c) in U.S. Pat. No. 7,174,203 B1, granted Feb. 6, 2007, for Method and System Relating to Monitoring and Characterizing Heart Condition. The contents of these three application and single patent documents are fully incorporated herein by reference.

BACKGROUND AND SUMMARY OF THE INVENTION

The present invention pertains to the field of acoustic cardiography, and more specifically focuses, within this field, on methodology for controlling cardio-assisted, pacemaker (implanted or external) pacing characteristics in relation to a pacemaker-equipped subject who is potentially at risk for ischemia and sudden, cardiac death—the former being potentially a key factor leading and contributing to the latter. The methodology is based on using, as pacemaker therapy-control values, what are referred to herein as acoustic cardiographic therapy (AC) values, which are calculated from certain, selected, acquired ECG-and-heart-sound-associated parameters. Those skilled in the art will recognize that this acoustic-cardiography field involves, as was just suggested, the cooperative, information-integration use of both ECG and heart-sound information—information which is processed in different ways to obtain, selectively, various important heart-functionality parameters that especially correlate to, and help one to understand, the behavior of a subject's heart which is relevant to the matters of status of potential, impending or present ischemia and the risk of sudden cardiac death. Such integration characterizes and underpins important aspects of the present invention which offers a unique approach for addressing these two, serious heart-disease, heart-failure issues. Heart-functionality parameters which are key factors in the practice of this invention are LDPT (S2-Q), % LVST, S3 strength, S4 strength, and % EMAT, with particular emphasis resting on LDPT (S2-Q) and % LVST each of which is based upon combined ECG and heart-sound information.

In connection with practice of the present invention, I have discovered that, among all five of the just-mentioned, important, heart-functionality parameters, LDPT and % LVST, employed differently (individually for LDPT, and combinedly with each other or with others of the five parameters, as will be explained below) in the calculation of AC values, offer a very high likelihood of predicting both the potential onset and or presence of ischemia, as well as the onset of sudden cardiac death.

In this regard, and considering a principal focus of the present invention, the mechanism(s) involved with ischemia and sudden cardiac death may be thought of in the following fashion. In connection with this discussion, one may wish to make reference to FIG. 3 in the drawings which illustrates progressive, time-based changes in heart functionality (pictured in relation to the two most significant heart-functionality parameters, LDPT and % LVST) leading, via dangerous changes occurring in ischemia, to sudden cardiac death. Once the heart becomes more ischemic, it stiffens, and it takes longer to fill during cardiac cycles. At the same time, ischemia can seriously damage the heart so much that the heart's pumping function also becomes impaired, and since the heart is required to maintain a subject's blood pressure, it has to pump longer and with greater difficulty to deal with a resulting, further impaired filling function. Since cardiac perfusion happens during diastolic filling, and mainly during the important S2-Q interval (LDPT), a serious, associated consequence is that the heart receives less of an oxygen supply under such circumstances. Under stress, this perfusion time can become impaired so much that even more heart muscle dies, and the overall victim ventricle becomes more vulnerable for lethal tachyarrhythmia—the key, and highly dangerous, event which results in so-called sudden cardiac death.

As will become apparent, practice of the present invention can provide effective early warnings which can preemptively counteract, or at least significantly impair and minimize, these two, related, dangerous heart conditions.

In connection with the importance, in practicing the instant invention, of using heart-sound information along with ECG information, the utility of ECG information in relation to detecting various heart-failure issues, such as those which concern the present invention, or to help significantly with the management of heart-failure patients, is extremely limited, since the relevant electrical information does not contain any mechanical information reflective of the heart's pumping function and filling dynamics. Accordingly, complementing ECG information with heart-sound information for monitoring heart-failure patients improves the utility of any methodology, and of any device, such as a Holter device, in terms of addressing the ischemia and sudden cardiac death risk categories of problems associated with heart disease.

For example, while ECG information, in particular when recorded during exercise stress, has clear utility in the detection and management of ischemic heart diseases, the relevant ECG parameters, like the ST segment depression, are not sensitive enough to enable ECG testing to stand alone as a test with respect to the diagnosis of the disease characteristics which are the concern of the present invention. As an illustration, a proper diagnosis of ischemia typically requires the utilization of several other kinds of tests, such as blood tests, stress echo tests, etc., in order to yield something approaching conclusive evidence of a potential or actual ischemia condition. Further, the utility of ECG information to detect ischemia is significantly reduced in relation to implanted monitors, due to the limited number of available ECG vectors, and the location of the relevant ECG leads. Additionally, for the electrical markers of ischemia to be specific, a significant amount of heart tissue has to have been previously compromised through the lack of oxygen supply, and thus, such markers often produce information which is actually—reflective of an in-place, aggressive and irreversible ischemia condition.

Heart sounds can complement the electrical markers made available by ECG information relating to ischemia in two different ways. One of these ways involves examining changes that take place in fluid dynamics during the filling phases of the ventricles to reveal an abnormally short, and therefore impaired, blood supply condition for the heart, before heart tissue is damaged and the relevant electrical markers become elevated in strength. In this context, principal cardio-functionality parameters which are very relevant include LDPT (S2-Q), % LVST, S3 strength, S4 strength, and EMAT, with, as mentioned above, key emphasis resting principally on LDPT (S2-Q) and % LVST—both directly involving combined ECG and heart-sound information. The second way involves a situation respecting conditions wherein (a) ECG electrical markers are confounded through the lack of a sufficient number of ECG leads, or because of poor ECG information quality, as well as in (b) situations where temporary tissue damage is not sufficient to elevate the relevant electrical ECG markers. Heart sounds will, in these circumstances, reflect the change in diastolic or even systolic function due to ischemia, and therefore will indicate the impact of the ischemic parts of the heart relative to the pumping and filling functions of the heart.

In this setting, while it will be very evident to those skilled in the art that the methodology of the present invention may be employed successfully in a number of different heart-failure, heart-pacing environments, a preferred and best-mode approach toward practicing the invention is disclosed herein, for illustration purposes, specifically in the context of biventricular, pacemaker pacing associated with the use of an otherwise conventional, portable/ambulatory, Holter monitoring and recording device—a context wherein the invention has been found to offer particular utility.

As will be seen from the detailed description of the invention which is presented below, the methodology of the invention is especially focused on addressing ischemia and sudden cardiac death risk issues involving an ambulatory, heart-failure patient who is equipped with either an internal or an external pacemaker, such as a biventricular pacemaker, along with a classic Holter device which is capable of (a) processing input information relating to pacemaker and heart activities, (b) storing relevant information, and (c), when associated with an appropriately algorithmically programmed digital computer (internal or external), responding to real-time, monitored heart behavior to perform controls and adjustments in the operation of the associated pacemaker.

More specifically, and as will be seen, implementation of the present invention focuses, on the development and defining (computer calculation) of what is referred to herein as an acoustic cardiographic therapy, or control, (AC) value (also referred to simply as an AC Value). This AC Value "entity", utilizing computer processing, is determined from (i.e., is based upon) one or more heart-functionality parameter(s) that are especially relevant to the ischemia and risk of sudden cardiac death issues. In this setting, the invention specifically recognizes the special utility, in different circumstances, of several, important heart-functionality parameters as bases for calculating, and then employing, AC Values that are deemed to be the most useful for controlling the pacing operation of a pacemaker, such as pacing rate, pacing strength and atrioventricular (AV) and interventricular (IV) delay times. These parameters are five in number. As mentioned earlier, they include LDPT (S2-Q), % LVST, S3 strength, S4 strength, and EMAT.

In certain circumstances, the LDPT (S2-Q) parameter may be used as an averaged singularity for AC-Value calculation purposes, or may be used in an averaged and mathematically combined condition along with % LVST. In certain other circumstances, an appropriate averaged and computed mathematical combination of the five parameters may be the best to use, always including at least one of LDPT (S2-Q) and % LVST. Other averaged, combinational choices are certainly possible, and those skilled in the relevant medical arts will understand how to choose AC-Value-basing parameters from the detailed description of the invention which is presented below. Non-exclusive illustrations of averaging and mathematical combining of heart-functionality parameter values involved in the calculation of AC values are given below.

DEFINITIONS

At this point, it will be useful to define certain terms and terminology which appear(s) in the text herein.

LDPT—Left ventricular diastolic perfusion time measured as the S2-Q time interval. FIG. 2 in the drawings clearly pictures this interval.

% LVST—Left ventricular systolic time measured as the time from the mitral component of the first heart sound to the aortic component of the second heart sound. % LVST is computed as LVST divided by the dominant RR interval (the time between two consecutive R waves determined in and from an ECG signal). % LVST indicates how much of the cardiac cycle is occupied by systole (pump function) versus diastole (filling). A normal % LVST value lies usually in the range of about 35% to about 45%.

S3 strength—The strength of the third heart sound based on the intensity and persistence of that sound. Conventionally, acoustic cardiography provides a value for S3 strength in the range of 1 to 10. If this value equals or exceeds 5.0, a conventional algorithm employed herein declares that a third heart sound is present. With relatively normal heart rates, the third heart sound occurs typically about 0.12- to about 0.16- seconds after the second heart sound. The most likely explanation for the production of the third heart sound is that vigorous and excessively rapid filling of blood into a stiff ventricle is suddenly halted, causing audible vibrations. In persons generally older than about 40-years, the third heart sound has been shown to indicate elevated filling pressure and systolic dysfunction. This S3 sound is associated with an abnormal diastolic filling pattern, and almost all persons with pseudonormal, or restrictive, filling patterns exhibit third heart sounds.

S4 strength—The strength of the fourth heart sound based on the intensity and persistence of that sound. Conventionally, acoustic cardiography provides a value for S4 strength in the range of 1 to 10. The fourth heart sound occurs after T-wave onset and before the first heart sound in a cardiac cycle. The S4 sound occurs as blood enters a relatively non-compliant ventricle late in diastole because of atrial contraction, resulting in vibrations of (a) the left ventricular muscle, (b) the mitral valve structure, and (c) the left ventricular blood mass often associated with left ventricular hypertrophy due to the decreased compliance and frequency present in acute myocardial infarction. The presence of the fourth heart sound is always abnormal.

EMAT—The electromechanical activation time measured from Q-wave onset (from ECG information) to the time of closure of the mitral valve within the first heart sound. The time value of EMAT reflects the time required for the left ventricle to generate sufficient force to close the mitral valve, and is therefore related to the acceleration of the pressure curve in the left ventricle.

AC Value—While other approaches may be made if desired, an AC Value herein, generally, is a computer-calculated, numeric value based upon simple, common-parameter averaging, and arithmetic combining (adding, subtracting, multiplying, etc. of the respective, common-parameter averages associated with plural, different parameters), of the determined values of user-selected parameters (one or more) drawn from the list of the five, heart-functionality parameters mentioned above, acquired over a user-selected, cardiac-cycle-collection time period, such as a ten-second time period.

As an illustration, if two heart-functionality parameters (as distinguished from a singular, selected-parameter situation), A and B, have been selected to form the basis for a calculated AC Value, the respective A and B values obtained from the plural heart cycles acquired during a given cardiac-cycle-collection time period are individually averaged to produce an average A value and an average B value. These two, average, parameter-specific values are then mathematically combined as desired, for example by addition, subtraction, multiplication, etc., to produce a resulting, usable AC Value. If desired, in such a plural-parameter use situation, weighted mathematical combining may be employed to recognize differential importances relating to the selected heart-functionality parameters.

Actual AC Value—an AC Value which is calculated, in real-time, based upon a selected number of cardiac cycles acquired from a subject during implementation and operation of the methodology of the invention.

Reference AC Value—an AC Value based upon one or more of the five, mentioned, selected heart-functionality parameters, determined from data acquired from a subject at one or more point(s) in time when that subject's heart appears to be operating in a normal and satisfactory manner. Such an AC Value may also be drawn from an available database of heart-functionality data derived from a selected population of people having characteristics which are deemed to be similar to those possessed by a particular subject.

In general terms, the present invention involves a method for assessing, and applying therapy in relation to, degree of ischemia heart and risk for sudden cardiac death in an ambulatory, therapy-device-equipped (illustration—pacemaker-equipped) subject utilizing a Holter-type instrumentality, of either the internal or external variety, through assessing the effectiveness of the subject's heart's pumping and filling functionality, with the method including the steps of (a) gathering simultaneous ECG-electrical and heart-sound-mechanical data, (b) following such gathering, computer processing and interrelating the gathered data especially (though not necessarily exclusively) to obtain the heart-functionality parameter LDPT (S2-Q), and possibly the % LVST parameter, and (c) thereafter, and effectively using the obtained LDPT (and possibly also the obtained % LVST), adjusting, as necessary, the subject's therapy device (for example, pacemaker) in a manner designed to cause the device to minimize and counteract the likelihood of at least one of the onset or advancement of ischemia, and the onset of sudden cardiac death.

In a more specific sense, this method is one wherein the mentioned computer processing involves (a), based on the obtained LDPT (and possibly % LVST), calculating an actual, real-time, acoustic cardiographic therapy (AC) value, (b) comparing such calculated, actual AC value to a pre-established, LDPT (and possibly % LVST)-based, reference AC value to detect differences therebetween, and (c) performing adjustment, as necessary, of the operating behavior of the therapy device so as to minimize such differences.

Another manner of expressing the methodology of the invention is to describe it as a method for assessing and controlling degree of ischemia and the risk for sudden cardiac death in an ambulatory, therapy-device-equipped patient utilizing a Holter-type instrumentality, of either the internal or external variety, through assessing the effectiveness of the patient's heart's pumping and filling functionality, with this view of the method including the steps of (a) gathering simultaneous ECG-electrical and heart-sound-mechanical data, (b) following such gathering, computer processing the gathered data to calculate an ischemia- and sudden-cardiac-death-relevant, acoustic cardiographic therapy (AC) value based upon ECG-electrical and heart-sound heart-functionality parameters, including either (1) a combination of LDPT (S2-Q) and % LVST, or a (2) combination of all of S3 strength, S4 strength, EMAT, % LVST, and LDPT (S2-Q), and (c) using the calculated AC value, applying therapy-device control in a manner designed to minimize and counteract the likelihood of at least one of the onset or advancement of ischemia, and the onset of sudden cardiac death.

As was suggested earlier herein, and in accordance with user wishes, other heart-functionality parameter combinations, may be used for the generation of AC values, with at least one of LDPT and % LVST always being included for use.

There are many other unique features and facets of the present invention, and these will surface in a more thorough understanding of the invention which will be obtained by reference to the below following detailed description of the preferred and best-mode embodiment of the invention in connection with the accompanying drawings.

DESCRIPTIONS OF THE DRAWINGS

FIG. 1 is a block/schematic diagram illustrating the overall methodology of the present rest-phase pacemaker control invention.

FIG. 2 (mentioned briefly above) is a time-based graphical waveform diagram focusing on the LDPT/S2-Q time interval which marks a representative, single heart-cycle LDPT parameter FIG. 3 (also mentioned briefly above) presents three, related, vertically stacked, common-time-base waveform graphs illustrating representative conditions in heart rate, % LVST (LVST/RR), and LDPT leading up to a fatal, sudden cardiac death event.

DETAILED DESCRIPTION OF THE INVENTION

Figure 5:
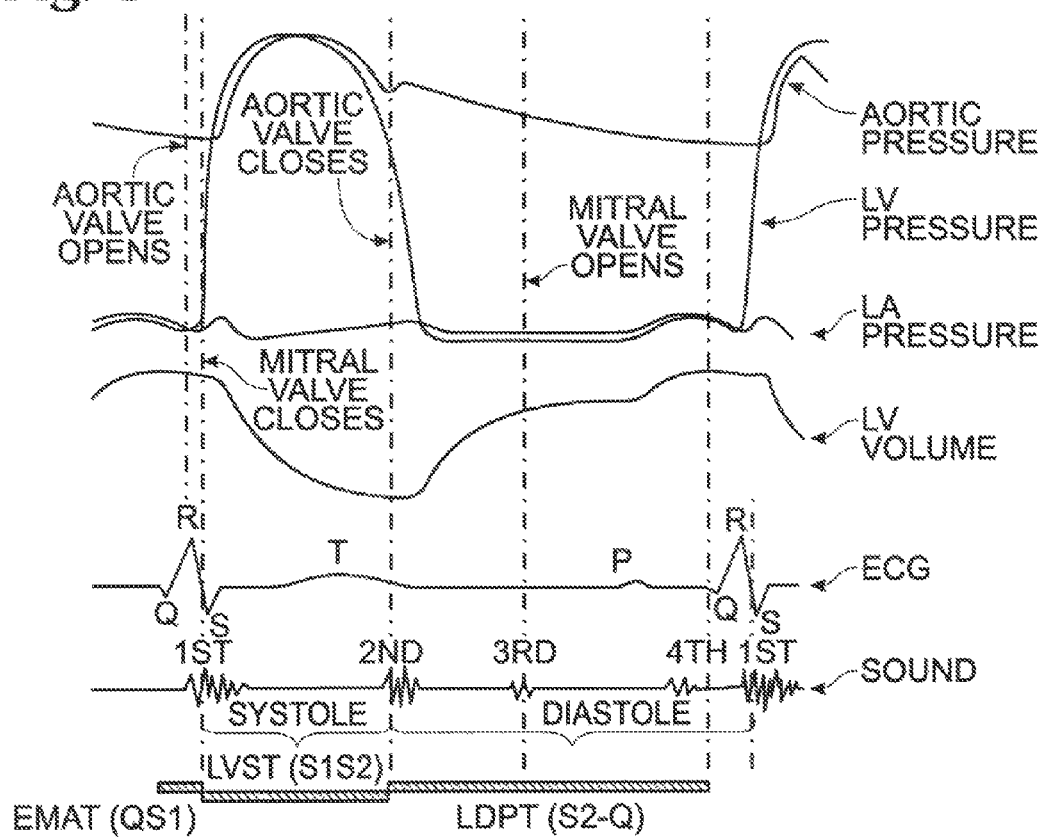
FIG. 5 is a comprehensive, graphical, time-based waveform presentation of ECG data, heart-sound data, certain heart functions, and aspects of several parameters which are relevant to practice of the present invention.

Turning now to the drawings, and beginning with FIG. 5, for those who are generally skilled in the relevant art, the content of the time-based graphical display which is presented in this figure is completely familiar, and requires no particular elaboration. As will be observed, this content plainly illustrates the characteristics of the several, particular, different heart-functionality (physiologic) parameters, both electrical and acoustical, which differentially play roles in the AC-Value calculating practice of the present invention. These parameters, whose respective definitional characteristics which are relevant herein have been set forth above, include LDPT, % LVST, S3 strength, S4 strength, and EMAT. How these parameters play roles in the practice of the invention will become apparent in the discussion which follows shortly below.

Figure 3:
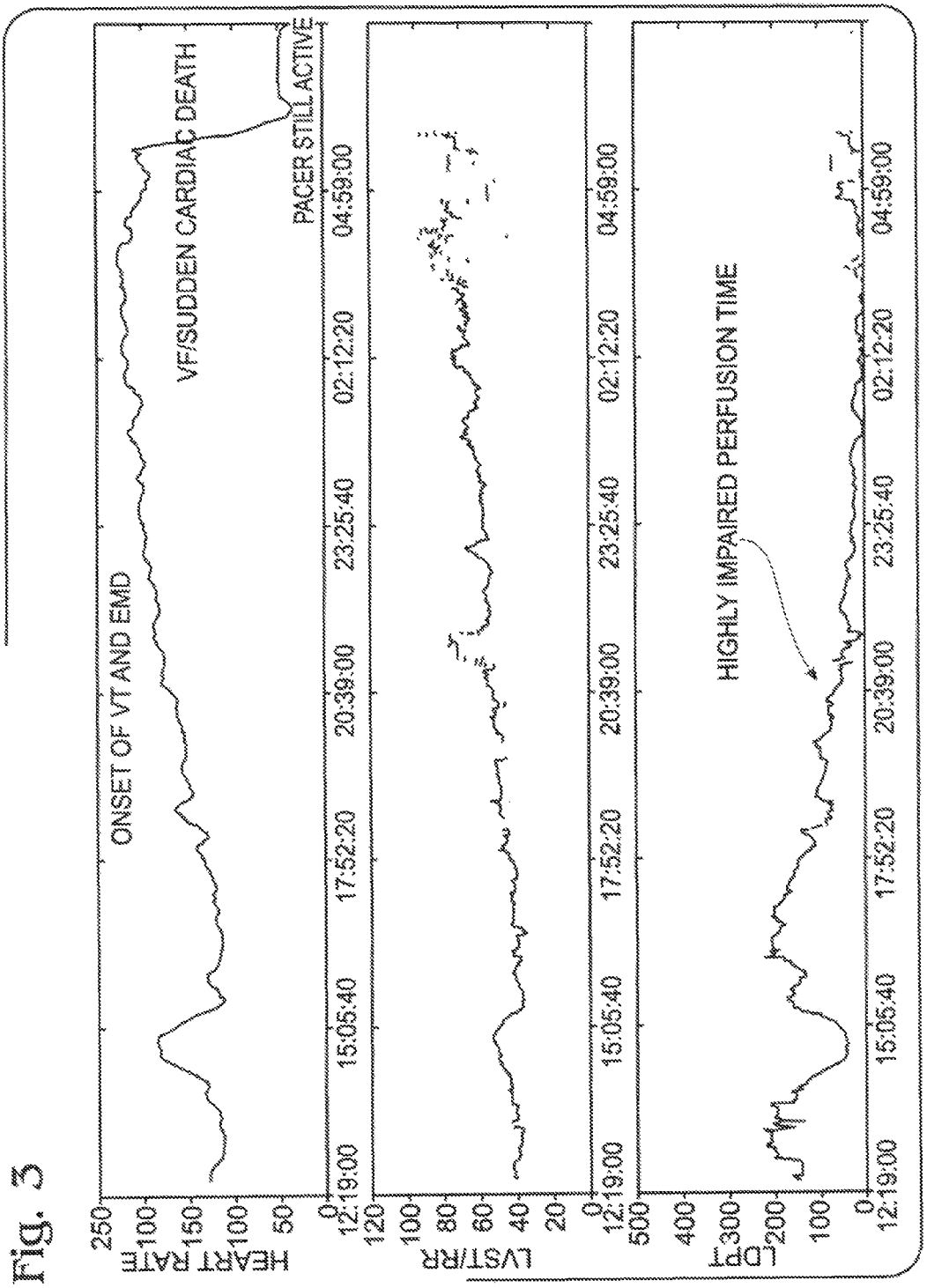
Figure 4:
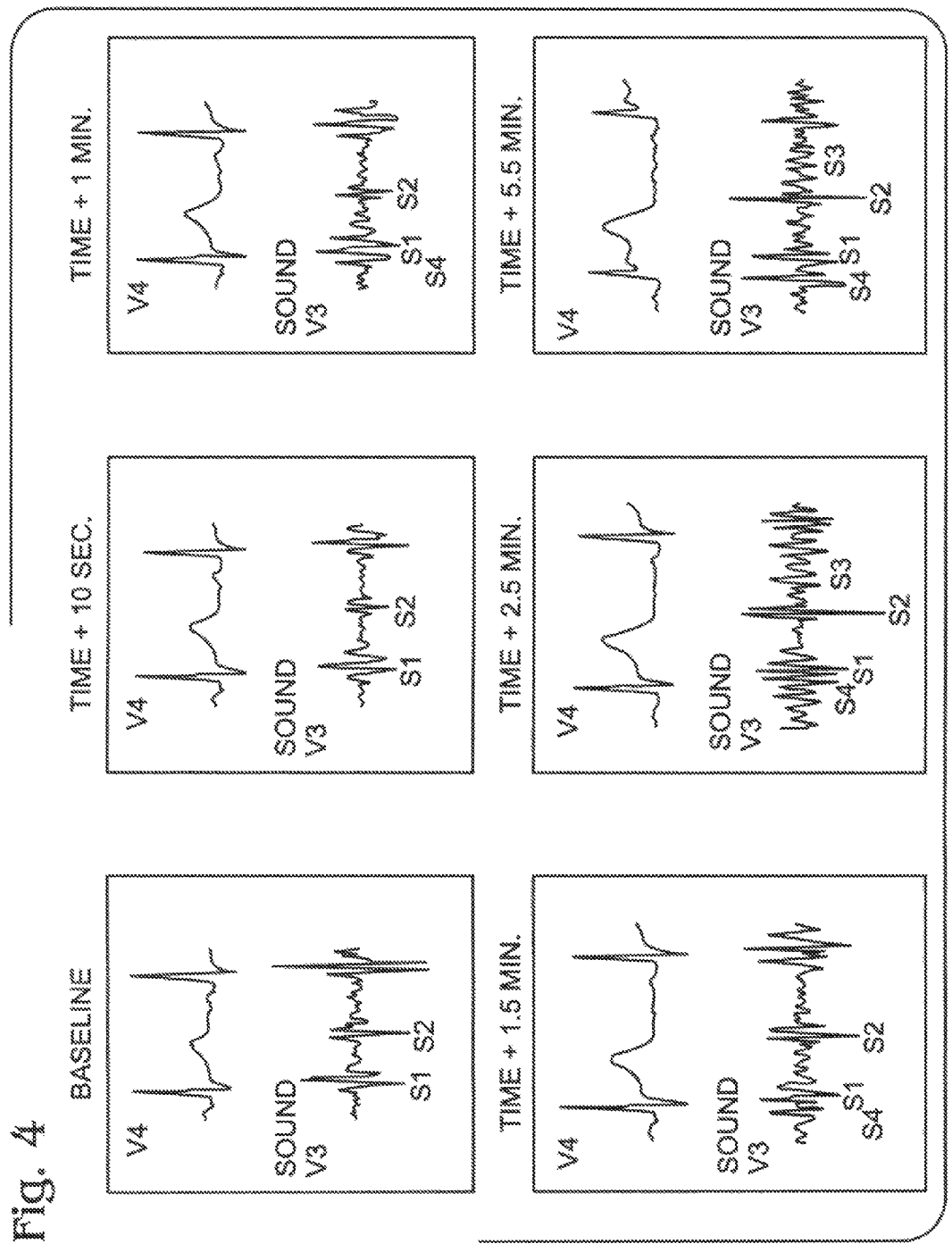
FIG. 4 illustrates six, time-successive (spaced), time-based and time-progressive, graphical representations of V4-site ECG information, and simultaneously acquired V3-site heart-sound information showing various trend changes in these two categories of data.

Focusing next, briefly, on FIGS. 2-4, inclusive, from the descriptions of these three figures which have been given above, and from the full and particularized description of the invention methodology which is presented below, these heart-parameter "context" and background-giving figures are quite self explanatory to those skilled in the relevant art. Accordingly, they are not discussed herein in detail. The reader should, however, freely refer to them as graphical illustrations that are useful in appreciating the operating environment of the invention.

Switching attention now to FIG. 1, indicated generally at 10 is a block/schematic diagram which illustrates the overall architectural layout, and the key features, of the methodology of the present invention. Methodology 10 is specifically illustrated and described herein in the context of a person—an "ambulatory" subject—(not specifically illustrated in the drawings) (a) who has a heart-failure (poor pumping and filling) condition, (b) who may have, or be about to have an ischemia condition, (c) who is at risk for sudden cardiac death, (d) who has been equipped with an otherwise conventional, ambulatory Holter monitoring and recording device, and (e) who has also been equipped with a heart-pacing device in the form of a biventricular pacemaker. Such Holter and heart-pacing devices may each be either an implanted (internal) device, or an external device, with respect to which the features of the present invention are equally applicable. However, for invention description purposes herein, an assumption is made that each such a device is of the implanted, internal category.

Continuing with a discussion regarding FIG. 1, shown more specifically at 10 are a preferred, and best-mode, embodiment of, and manner of practicing, the methodology of the present invention. As shown in this figure, methodology 10 is illustrated in an arrangement which includes nine blocks 12, 14, 16, 18, 20, 22, 24, 26, 28. These blocks are operatively interconnected by information and/or control communication connections represented by arrow-headed lines 30, 32, 34, 36, 38, 40, 42, 44. Also included in FIG. 1 are a bracket 46 which represents the mentioned, non-illustrated-subject's heart, and a bracket 48 which, in relation to blocks 16, 18, 24, 26, 28 below it, combinedly represents both an ambulatory, implanted Holter device, and an associated, appropriately, and conventionally, algorithmically programmed digital computer, which is preferably also an implanted structure.

Algorithmic programming in this computer, which programming includes an architecture that is suitable for implementing and handling all of the still-to-be-described (a) monitoring receiving, (b) AC-value-calculating, (c) AC-value-comparing, (d) pacemaker (therapy device) controlling, (e) information storing, (f) trend evaluating, (g) information transmitting, and (h) alarming and calling, tasks, as well as any other computational/information-management tasks that may be desired, may be structured in various different, entirely conventional ways that are all well within the skills, knowledge and understanding possessed by those generally skilled in such programming arts. This condition of readily understandable programming which is suited to the practice of the present invention is especially made clear in the contexts of the teachings of FIG. 1 of the drawings presented herein, and of the operational description of the invention set forth below. Accordingly, programming details, and details of related algorithmic architecture associated with, and installed in, the computer represented by bracket 48, which details form no part of the present invention, are not elaborated herein.

Blocks 12, 14 represent conventional ECG and heart-sound collection/acquisition structures and methods, respectively, which are associated conventionally with gathering and communicating, from the subject's heart 46 to the Holter device represented by bracket 48, ECG and heart-sound information. This ECG and heart-sound information (heart-functionality information) is delivered through the Holter device, effectively from blocks 12, 14, respectively, to block 16 (which is within the computer, and is labeled "Process to Obtain AC Parameter Information") via communication connections 30, 32, respectively. More will be said shortly about block 16. AC Parameter Information is also referred to herein as AC Value information, or simply by the term AC Value.

One should note at this point that the present invention is not concerned with any specific manner or manners in which such heart-functionality information is acquired, and, accordingly, no specific details of such acquisition are set forth herein. Suffice it to say that each "event" of gathering such information takes place over a user-selectable, pre-determined, and pre-computer-programmed interval of time which is sufficient to permit the capture of heart data from a plurality of real-time, i.e., current, cardiac cycles. For the purpose of illustration herein, an assumption is made, for invention-disclosure purposes, that, under the control of the employed computer, ten such cycles are acquired to obtain a ten-heart-cycle collection of heart data, although it is clearly recognized that different specific numbers of information-collection cycles may be employed in relation to the acquisition of a given collection. To the extent that the term "information-collection cycle" is employed herein, it is meant to refer to such a collection of ten cardiac cycles. The rate, or frequency, of successive ten-cycle data-collection events is a matter of user choice, and is suitably programmed into the mentioned digital computer.

Continuing with a general description of FIG. 1, connection 34 connects block 16 to block 18, labeled "Apply Control or Other", which block (18) is, in turn, connected by way of connections 36, 38 to blocks 20, 22, respectively.

Block 20, labeled "Therapy Device" is herein the earlier-mentioned biventricular pacemaker. Connection 36 functions, as will soon be described, to apply effectively from, and as determined by, blocks 16, 18 to the pacemaker control signals designed to modify, as necessary, the pacemaker's then-current operating condition in response to information developed by the computer in the operations of blocks 16, 18. Such signals variously affect the pacemaker's operating condition preferably in relation to one or more of (a) pacing rate, (b) pacing intensity, (c) arterio-ventricular (AV) delay, and (d) inter-ventricular (IV) delay.

Pacemaker 20 is appropriately and conventionally, internally connected to the subject's heart, 46, for the purpose of applying controlled pacing therapy to the heart in accordance with whatever is the then specific operating status or condition of the pacemaker, such being under the control of the mentioned computer, and its functional and structural blocks 16, 18. This conventional, internal, pacemaker pacing connection is not illustrated in FIG. 1.

Block 22 represents an optional practice of the invention with respect to which a "Control" or "Other" condition specifically associated with the performance of blocks 16, 18 is employed, in accordance with user predetermination as programmed into the associated computer, to trigger some form of immediate outgoing notification, such as an alarm, a telephone call, or some form of alarm-condition recording of data.

Block 24, marked "Store", which is connected to block 16 via communication connection 40 takes the form of a memory location within the mentioned computer, wherein various values, including, in accordance with a user's selection, AC Values, and/or heart-functionality parameters, per se, may be stored for such additional purposes as those that are represented, respectively, by blocks 26, 28. More especially, block 26, labeled "Evaluate Trends", which is coupled to block 24 through communication connection 42, represents computer structure and functionality in the mentioned computer for noting and evaluating time-based trends which take place in obtained and calculated AC Values, and heart-functionality parameters. Aspects of such trend data are pictured in FIG. 4.

Block 28, labeled "Transmit", which is coupled to block 24 through communication connection 44, functions, in accordance with an option provided by the present invention—in particular, an option one which is implemented under the control of the mentioned computer—for transmitting in any suitable fashion to a remote receiving location (not specifically shown), such as to the office of selected medical personnel, various portions of stored data to be used in a variety of ways which are not related to the features of the present invention.

Describing now the practice of the methodology of the present invention, through blocks 12, 14 and Holter 48, and through the Holter the associated digital computer (also represented by reference numeral 48, continually receive(s) from heart 46 a flow of heart-functionality data in the forms of ECG and heart sound information. In accordance with user-determined programming established in the computer, and at a data-gathering rate established by such programming, block 16 recurrently receives and computer-processes successive, ten-heart-cycle, information-collection cycles of this ECG and heart-sound information to identify therein and calculate for each cardiac cycle per-cardiac-cycle values for whichever one or ones of the five, above-identified, heart-functionality parameters has(have) been chosen by a user to be employed in the practice of this invention ultimately for effecting pacing control over the operation of pacemaker 20.

For the purpose of ongoing description of the invention methodology herein, and just for single-illustration purposes, we will further assume, at least initially, that the parameter LDPT (see especially FIG. 2) has been chosen as a singularity to form the basis for pacemaker-operation control in relation to the issues of assessing degree of ischemia and of risk for sudden cardiac death, and in accordance with the invention, and within block 16, a computer calculation is thus performed for each information collection cycle of heart data to generate an actual, relevant AC Value through a process of simple averaging of the several collected and calculated LDPT values drawn from each of the collected, ten-cardiac-cycle streams of heart-behavior data. This calculated, actual AC Value is supplied, internally in the computer, to a programmed data-comparison "portion" of the computer. Such a calculated, real-time AC Value constitutes herein an assessment of degree of ischemia and of risk for sudden cardiac death.

Also pre-programmed into and stored in the computer in accordance with user direction is a selected, user-desired and selected reference AC Value which is suitably based upon the LDPT heart-functionality parameter. This reference AC Value is also supplied to the just-mentioned data-comparison portion of the computer, and therein a comparison takes place between each just-mentioned, calculated, real-time, actual AC Value with the user-selected, reference AC Value.

The general definition of reference AC Value has, of course, been provided earlier herein. For the purpose of ongoing description of the methodology of the invention, we will assume that this reference value has been based upon previously acquired, real-time heart-functionality data derived directly from the subject, per se, during a prior span of time when medical personnel have determined that the subject's heart is performing in normal and satisfactory pumping and filling manners.

From the comparison which thus takes place, any difference which is detected between the actual AC Value, as calculated, and the stored, reference AC Value which is chosen to be used, is noted and supplied to block 18 via communication connection 34. The AC-Value difference information, if any, which is passed by way of connection 34 to block 18 causes block 18 to send, by way of communication connection 36, to pacemaker 20 a control signal, or signals, which effect(s) an operational adjustment, or adjustments, as necessary, to re-form the pacing operation of the pacemaker so as to stimulate heart 46 in a manner intended to minimize the difference between a calculated, current, actual AC Value and the just previously chosen-for-comparison, relevant, reference AC Value. The preferred operational adjustments take the form of specific adjustments that are made in one or more of the pacing rate, the pacing intensity, the AV delay, and the IV delay operational behavior(s) of the pacemaker.

This adjustment, of course, is aimed at furnishing heart therapy from pacemaker 20 which is deemed most appropriate for improving the pumping and filling behaviors of heart 46, and especially for inhibiting, if not completely preventing (an ideal), the serious problems of onset or progression of ischemia, and of risk for sudden cardiac death.

This activity recurs for each data collection cycle, with AC-Value comparisons made, and pacemaker operational-status adjustments performed, as necessary, to cause, as nearly as possible, calculated, real-time AC Values and the reference AC Value to match. Such is true no matter which one or more of the five relevant heart-functionality parameters has been chosen to use for assessment and pacemaker control purposes.

Thus, throughout the time of Holter and pacemaker operation—day (ambulatory time) and night—and in accordance with the unique methodology of the present invention, recurrent heart-functionality monitoring, and calculating of actual AC Values, based on specially recognized, featured and selected heart functionality parameters, take place, followed by respective comparison activities in the relevant computer, as explained, thereby to produce effective operational control adjustments as needed which are delivered as control signals by block 18 to the pacemaker in a continual feedback effort to maintain, as closely as possible, an equality of actual and reference AC Values. As was mentioned earlier, the frequency of recurrent monitoring, and of associated, actual AC Value calculations, and actual and reference AC-Value comparisons, is a matter of user choice, and is programmed appropriately into the employed computer.

Completing now a description of what is shown in FIG. 1, in accordance with pre-determination made by the user of the methodology of the invention, the employed digital computer is suitably programmed to capture and store selected AC and/or heart-functionality-parameter value data in memory block 24 for subsequent employment particularly in two different modes of use which are represented, respectively, by blocks 26, 28. More specifically, and as an illustration, in relation to a suitable request placed by a user, stored information from memory block 24 is furnished via connection 42 to block 26 which represents a performance by the relevant computer to evaluate, and in any suitable fashion to present for review, different trends, such as AC value trends, and/or various heart-functionality parameter trends. As was mentioned earlier herein, FIG. 4 in the drawings illustrates a representative, visual, graphical result presentation of such a trend evaluation. Specifically, it shows six, specific trend-data illustrations, reflecting six, different moments in time. This information, of course, is useful to medical personnel in terms of further evaluating a subject's heart condition, and perhaps in determining various kinds of additional therapies and/or responses to noted heart-trend information.

In another manner of employing information stored in memory block 24, either under pre-programmed planning, and/or as a consequence of a specific user request, certain stored data may be communicated via connection 44 to block 28 which represents any suitable data-transmission instrumentality, such as a radio instrumentality or the Internet, for transmitting selected, stored data to some remote location, such as to a physician's office (not specifically shown in the drawings).

Finally, and discussing an operation which may be performed in relation to activities taking place within computer block 18, the system and methodology of the invention may be called upon in any suitable fashion to supply, over connection 38 to block 22, some form of an outwardly presentable heart condition or event notification, such as an emergency alarm, a telephone call to a specific recipient or, a readable recording.

The present invention thus proposes a unique heart-pacing-device control methodology. This methodology may be expressed as a method for assessing, and applying therapy in relation to, degree of ischemia and risk for sudden cardiac death in an ambulatory, therapy-device-equipped subject utilizing a Holter-type instrumentality, of either the internal or external variety, through assessing the effectiveness of the subject's heart's pumping and filling functionality, with this method including the steps of (a) gathering from the subject simultaneous ECG-electrical and heart-sound-mechanical data, (b) following such gathering, computer processing and interrelating the gathered data to obtain the heart-functionality parameter LDPT (S2-Q), and (c) thereafter, and effectively using the obtained LDPT, adjusting, as necessary, the subject's therapy device in a manner designed to cause the device to minimize and counteract the likelihood of at least one of the onset or advancement of ischemia, and the onset of sudden cardiac death.

The method further may be described as one wherein the mentioned computer processing involves (a), based on the obtained LDPT, calculating an actual, real-time, acoustic cardiographic therapy (AC) value, (b) comparing such calculated, actual AC value to a pre-established, LDPT-based, reference AC value to detect differences therebetween, and (c) performing adjustment, as necessary, of the operating behavior of the therapy device so as to minimize such differences.

The invention may yet further be described as method for assessing, and applying therapy in relation to degree of ischemia and risk for sudden cardiac death in an ambulatory, pacemaker patient utilizing a Holter-type instrumentality, of either the internal or external variety, through assessing the effectiveness of the patient's heart's pumping and filling functionality, including, as steps, (a) gathering simultaneous ECG-electrical and heart-sound-mechanical data, (b) following such gathering, computer processing and interrelating the gathered data to obtain the heart-functionality parameter LDPT (S2-Q), and (c) thereafter, and effectively using the obtained LDPT, adjusting, as necessary, the subject's pacemaker in a manner designed to cause the pacemaker to minimize and counteract the likelihood of at least one of the onset or advancement of ischemia, and the onset of sudden cardiac death.

In still other language, the invention may be viewed as a method for assessing and controlling degree of ischemia and the risk for sudden cardiac death in an ambulatory, therapy-device-equipped patient utilizing a Holter-type instrumentality, of either the internal or external variety, through assessing the effectiveness of the patient's heart's pumping and filling functionality, and featuring as steps (a) gathering simultaneous ECG-electrical and heart-sound-mechanical data, (b) following such gathering, computer processing the gathered data to calculate an ischemia- and SCD-relevant, acoustic cardiographic therapy (AC) value based upon ECG-electrical and heart-sound heart-functionality parameters, including S3 strength, S4 strength, EMAT, % LVST, and LDPT (S2-Q), and (c) using the calculated (AC) value, applying therapy-device control in a manner designed to minimize and counteract the likelihood of at least one of the onset or advancement of ischemia, and the onset of sudden cardiac death.

Other manners of expressing the methodology of the invention are presented below in the claims to invention.

Preferably, although not necessarily, all structure, firmware and software which are relevant to the practice of the invention, including a programmable digital computer with an appropriate memory, and all operational algorithmic software, are effectively "onboard" and installed as "component parts/aspects" of the pacemaker which is employed.

Accordingly, while a preferred and best-mode embodiment of, and manner of practicing the invention, and certain modifications thereof, have been illustrated and described herein, it is appreciated that further variations and modifications may be made in the practice of the invention within its scope, and without departing from its spirit.

I claim:

1. A method employable with an ambulatory, therapy-device-equipped subject who is utilizing a Holter-type instrumentality, for assessing, and applying therapy regarding, that subject's degree of cardiac ischemia and risk for sudden cardiac death via examining the subject's associated heart-functionality LDPT (S2-Q) and % LVST parameter information, said method comprising gathering from the subject simultaneous ECG-electrical and heart-sound-mechanical data, following said gathering, computer processing and interrelating the gathered data to obtain information regarding the subject's heart-functionality parameters known as LDPT (S2-Q) and % LVST as such parameter information is derived from the gathered data, and thereafter, using the obtained and derived subject's LDPT (S2-Q) and % LVST parameter information, adjusting, as necessary, the subject's therapy device in a manner designed to cause the device to minimize and counteract the likelihood of at least one of the onset or advancement of ischemia, and the onset of sudden cardiac death.

2. The method of claim 1, wherein said computer processing involves (a), based on the obtained LDPT (S2-Q) and % LVST heart-functionality parameter information, calculating an actual, real-time, acoustic cardiographic therapy (AC) value, (b) comparing such calculated, actual AC value to a pre-established, LDPT (S2-Q) and % LVST heart-functionality parameter information-based, reference AC value to detect differences therebetween, and (c) performing adjustment, as necessary, of the operating behavior of the therapy device so as to minimize such differences.

3. The method of claim 2 which further comprises repeating over time the steps associated with calculating an AC value so as to obtain plural, time-distributed, calculated AC values, and storing, in computer-accessible memory for future reference, at least certain ones of those plural values and/or the obtained and derived subject's LDPT (S2-Q) and % LVST heart-functionality parameter information.

4. The method of claim 3 which further includes evaluating, over time from stored AC values, the trend or trends of those values.

5. The method of claim 1, wherein said gathering further comprises computer processing the gathered data to calculate an ischemia- and sudden-cardiac-death-relevant, acoustic cardiographic therapy (AC) value based upon ECG-electrical and heart-sound heart-functionality parameters, including S3 strength, S4 strength, EMAT, % LVST, and LDPT (S2-Q), and using the calculated (AC) value, applying therapy-device control in a manner designed to minimize and counteract the likelihood of at least one of the onset or advancement of ischemia, and the onset of sudden cardiac death.

6. The method of claim 5 which further comprises repeating over time the steps associated with calculating an AC value so as to obtain plural, time-distributed, calculated AC values, and storing, in computer-accessible memory for future reference, at least selected ones of those plural values and/or the heart-functionality parameters.

7. The method of claim 6 which further includes evaluating, over time from stored AC values, the trend or trends of those AC values and parameters.

8. The method of claim 7 which further comprises transmitting selected aspects of the calculated and/or stored parameter and AC-value information to a remote receiver.

* * * * *